(12) United States Patent
Yonezawa et al.

(10) Patent No.: US 8,699,774 B2
(45) Date of Patent: Apr. 15, 2014

(54) IMAGE PROCESSING APPARATUS, CONTROL METHOD THEREOF, AND PROGRAM

(75) Inventors: Keiko Yonezawa, Kawasaki (JP); Yasufumi Takama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 334 days.

(21) Appl. No.: 13/050,287

(22) Filed: Mar. 17, 2011

(65) Prior Publication Data

US 2011/0243415 A1 Oct. 6, 2011

(30) Foreign Application Priority Data

Mar. 31, 2010 (JP) ................................. 2010-083401

(51) Int. Cl.
*G06K 9/00* (2006.01)
(52) U.S. Cl.
USPC .......................................................... 382/131
(58) Field of Classification Search
USPC .................. 382/128, 131; 128/922; 378/4, 21
See application file for complete search history.

(56) References Cited

U.S. PATENT DOCUMENTS

| 6,030,079 | A | 2/2000 | Torii | |
|---|---|---|---|---|
| 2007/0285619 | A1* | 12/2007 | Aoki et al. | 351/206 |
| 2009/0268159 | A1* | 10/2009 | Xu et al. | 351/206 |
| 2010/0118132 | A1* | 5/2010 | Yumikake et al. | 348/78 |
| 2010/0166280 | A1* | 7/2010 | Endo et al. | 382/131 |

FOREIGN PATENT DOCUMENTS

JP 11-151206 A 6/1999

OTHER PUBLICATIONS

Moriyama et al ("Meticulously Detailed Eye Region Model and Its Application to Analysis of Facial Images", IEEE Transactions on Pattern Analysis and Machine Intelligence, vol. 28, No. 5, May 2006).*
Srivasan et al ("Ultrahigh-Speed Optical Coherence Tomography for Three-Dimensional and En Face Imaging of the Retina and Optic Nerve Head", Investigative Ophthalmology & Visual Science, Nov. 2008, vol. 49, No. 11).*

* cited by examiner

*Primary Examiner* — Jason M Repko
*Assistant Examiner* — Shervin Nakhjavan
(74) *Attorney, Agent, or Firm* — Fitzpatrick, Cella, Harper & Scinto

(57) ABSTRACT

An image processing apparatus includes: a storage unit configured to store tomographic images in relation to the fundus of an examined eye; a detection unit configured to detect a boundary of retinal pigment epithelium and an inner limiting membrane from each of the images and to detect a part where the boundary is discontinuous; a determination unit configured to determine a surface of a sclera model for each of the images by use of the detected boundary and the inner limiting membrane; a generation unit configured to generate a sclera model including an optic papilla periphery by use of the surface of the sclera model and the part where the boundary is discontinuous; a combining unit configured to combine each of the images and the sclera model to generate a combined image; and a display unit configured to display the combined image generated by the combining unit.

24 Claims, 7 Drawing Sheets

IMAGE PROCESSING APPARATUS, CONTROL METHOD THEREOF, AND PROGRAM

BACKGROUND OF THE INVENTION

1. Field of the Invention

The present invention relates to an image processing apparatus that captures tomographic images of an observation target, a control method of the image processing apparatus, and a program, and particularly, to a technique applicable to observation of tomograms of an eye portion.

2. Description of the Related Art

In recent years, an apparatus that obtains tomograms of a retina by Optical Coherence Tomography (hereinafter, called "OCT") is implemented in clinical sites of ophthalmology, and new findings are provided. A plurality of tomograms of the retina can be obtained as volumetric images, and changes of each layer associated with the progression of disease can be quantitatively obtained across a wide range. This is expected to lead to highly accurate recognition of the degree of progression or evaluation of the treatment effect.

The relationship with the findings obtained by conventional methods is important to effectively utilize the images taken by the new apparatuses. For example, it is known that changes in the thickness of a nerve fiber layer are important in the diagnosis of glaucoma or in the evaluation of the treatment. Therefore, a C/D ratio (ratio of the cup and disc) obtained by fundus observation based on a slit lamp or a fundus picture is used as one of the effective indices.

Although three-dimensional information can be obtained by the observation based on the slit lamp, quantitative evaluation is difficult. On the other hand, although quantitative evaluation is possible in the fundus picture, three-dimensional information is lost. Therefore, Japanese Patent Laid-Open No. 11-151206 proposes a method related to acquisition and display of a shape of optic papilla using a stereoscopic fundus camera to obtain both the three-dimensional information and the quantitative evaluation. A method of approximately calculating the C/D ratio from the volumetric images obtained by the OCT is also proposed.

However, the information obtained by imaging by the stereoscopic fundus camera is just a combination of images obtained by capturing from different angles, and the information does not include tomographic information inside the retina. Therefore, there is a problem that the information inside the retina cannot be accurately obtained, as compared to the information of the volumetric images obtained by the OCT.

Furthermore, although detailed information can be obtained in relation to the nerve fiber layer, or the cup, in the OCT volumetric images, only approximate values can be obtained in relation to the sclera, or the disc. Therefore, in the conventional OCT volumetric images, it is difficult to present information that allows recognition of the entire image.

SUMMARY OF THE INVENTION

To solve the problems, one aspect of the present invention provides a technique of using a plurality of image data to present information that allows recognition of the entire image inside the retina.

An aspect of the present invention provides an image processing apparatus comprising: a storage unit configured to store a plurality of tomographic images in relation to a fundus of an examined eye of a patient; a detection unit configured to detect a boundary of retinal pigment epithelium and an inner limiting membrane from each of the plurality of tomographic images and to detect a part where the boundary of the retinal pigment epithelium is discontinuous; a determination unit configured to determine a surface of a sclera model for each of the plurality of tomographic images by use of the boundary of the retinal pigment epithelium and the inner limiting membrane; a generation unit configured to generate a sclera model including an optic papilla periphery by use of the surface of the sclera model and the part where the boundary of the retinal pigment epithelium is discontinuous; a combining unit configured to combine each of the plurality of tomographic images and the sclera model to generate a combined image; and a display unit configured to display the combined image generated by the combining unit.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

First Embodiment

Hereinafter, a first embodiment will be described with reference to the drawings. An image processing apparatus according to the present embodiment presents volumetric images that clarify the progression of disease when a plurality of volumetric images indicating temporal changes of glaucoma are obtained by OCT to observe detailed structural changes in the retina. Specifically, information at an initial stage of disease with high approximation accuracy based on OCT volumetric images is used to create a model of the sclera with few changes associated with the progression of disease. The model is combined with a plurality of volumetric images after the progression of disease and is displayed. As the created OCT volumetric images are used, the changes in the detailed structure of the retina associated with the progression of disease are clarified by displaying the changes with information of the disc, which serves as a comparison index of the changes.

Figure 1:
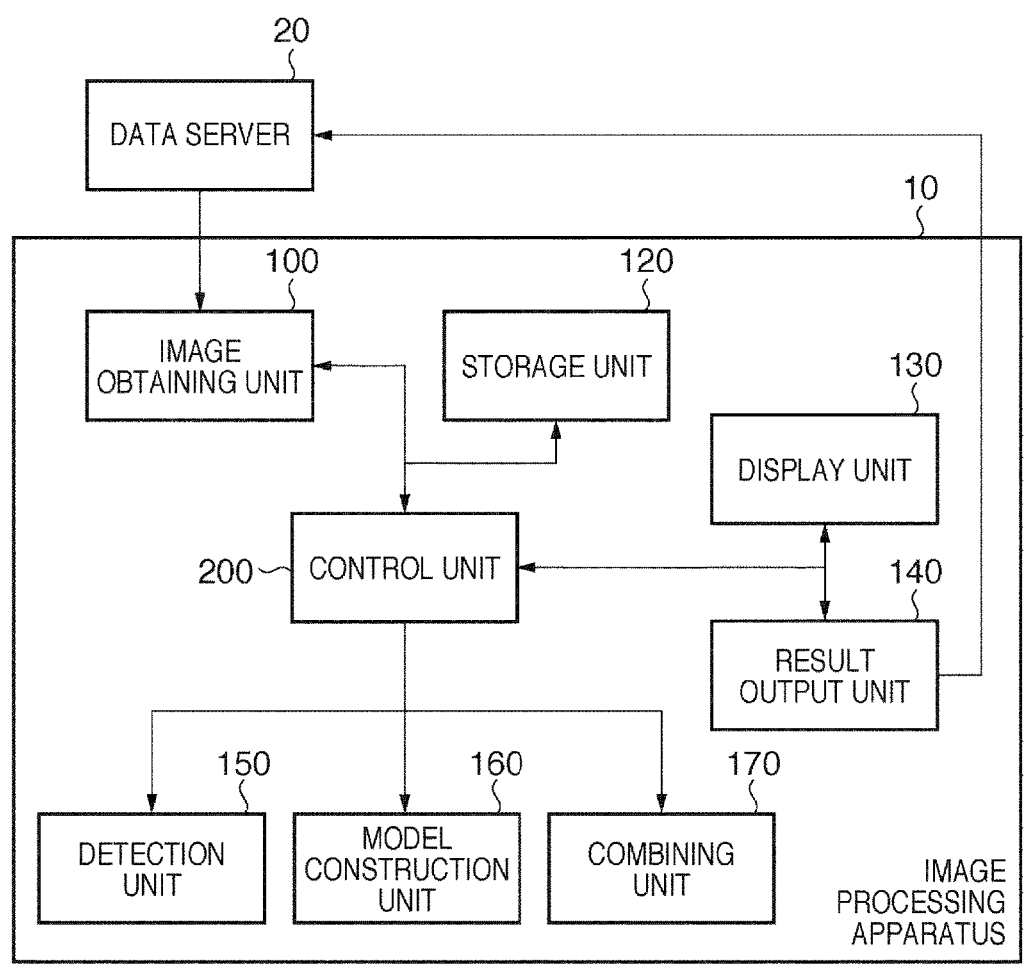
FIG. 1 is a diagram showing an exemplary functional configuration of an image processing apparatus according to a first embodiment.

FIG. 1 is a diagram showing an example of configuration of an image processing apparatus 10 according to the present embodiment. The image processing apparatus 10 includes an image obtaining unit 100, a storage unit 120, a display unit 130, a result output unit 140, a detection unit 150, a model construction unit 160, a combining unit 170, and a control unit 200. The image processing apparatus 10 is connected to an external data server 20.

The image obtaining unit 100 obtains a plurality of OCT volumetric images stored in the data server 20. The storage unit 120 stores image data of the obtained OCT volumetric images. The control unit 200 includes a CPU, not shown, and issues instructions for the operations of the components 100 to 170 constituting the image processing apparatus 10 to manage the control of the entire image processing apparatus 10. The display unit 130 displays the OCT volumetric images, etc., based on the instructions from the control unit 200.

The result output unit 140 saves image data, such as displayed OCT volumetric images, in the data server 20. The detection unit 150 extracts a retinal layer region from the image data of the OCT volumetric images to segment layers and detects retinal pigment epithelium (hereinafter called "RPE"), a boundary below the RPE (hereinafter, called "RPE boundary"), and a part (hereinafter, called "RPE end") where the RPE boundary is discontinuous around the papilla. The model construction unit 160 constructs a model of sclera from the boundary of RPE and the RPE end detected by the detection unit 150. The combining unit 170 combines the model of sclera constructed by the model construction unit 160 with the OCT volumetric images.

Figure 2:
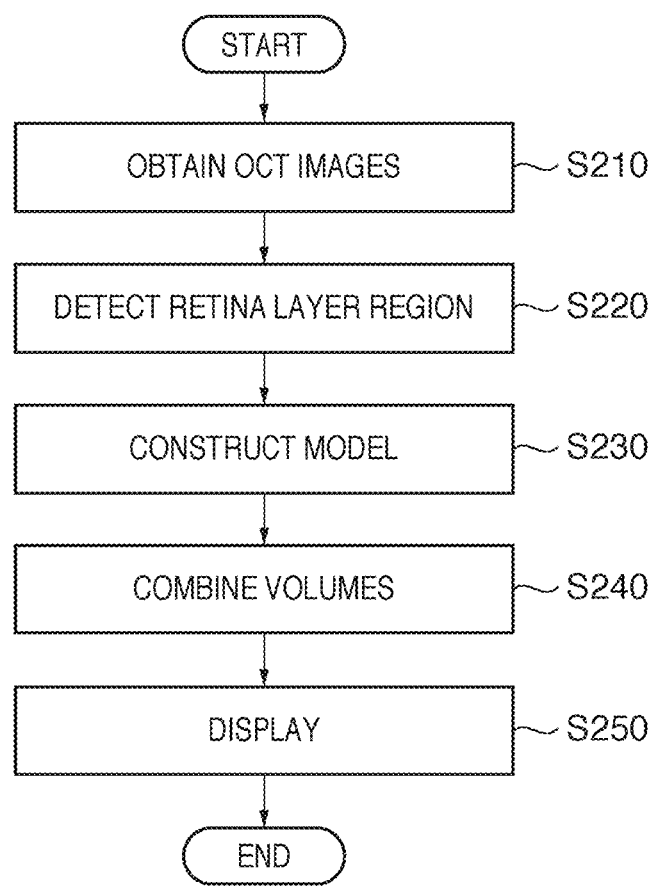
FIG. 2 is a flow chart showing an exemplary processing procedure of the image processing apparatus according to the first embodiment.
Figure 3:
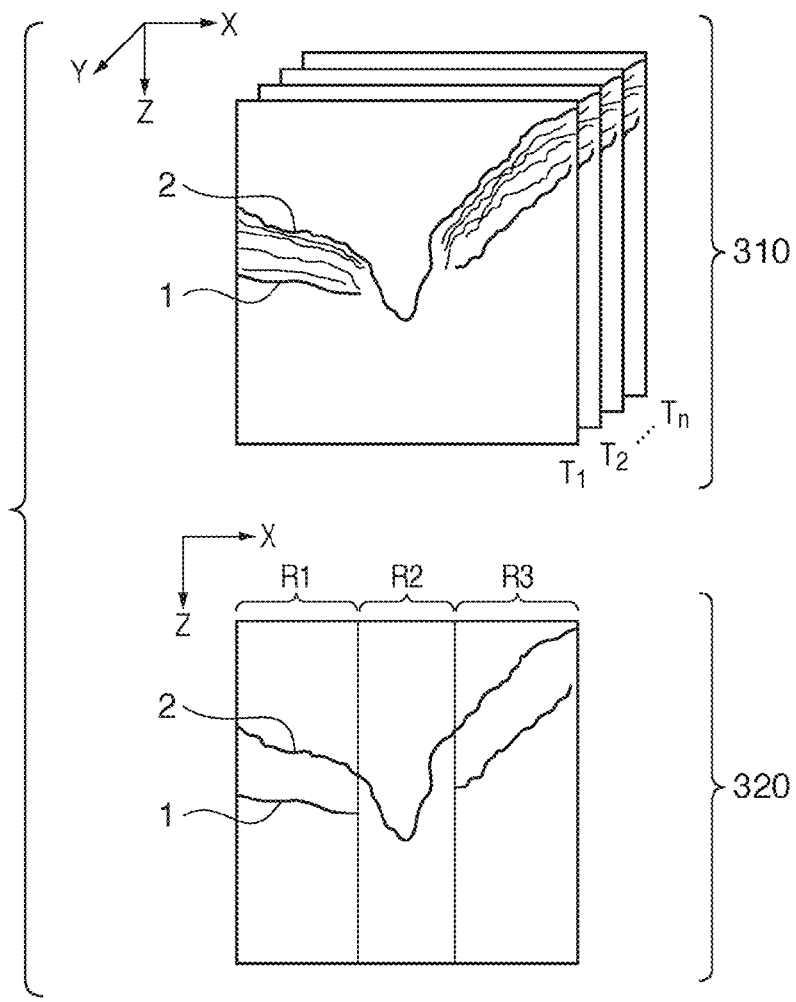
FIG. 3 is a diagram showing an example of volumetric images obtained by OCT.

FIG. 2 shows an exemplary processing procedure of the image processing apparatus 10 of the present embodiment. FIG. 3 is an exemplary schematic diagram of tomograms of optic papilla of retina captured by the OCT. The tomograms of optic papilla of retina and the processing procedure of the image processing apparatus 10 will be described with reference to FIGS. 2 and 3. In S210, the image obtaining unit 100 obtains a plurality of OCT volumetric images taken by the OCT from the data server 20, obtains images of an eye portion as volumetric images including sets of a plurality of two-dimensional tomographic images, and stores the images in the storage unit 120.

FIG. 3 shows an example of the images. In 310 of FIG. 3, $T_1$ to $T_n$ denote two-dimensional tomographic images (B scan images, hereinafter called "tomograms"). In each tomogram $T_k$, the horizontal direction of the tomogram will be defined as an X-axis direction, and the depth direction will defined as a Z-axis direction (hereinafter, a scan in the X-axis direction will be called "A scan lines"). In the tomogram $T_1$, reference numeral 1 denotes a boundary of the RPE, and reference numeral 2 denotes an inner limiting membrane. It is assumed that the volumetric images of the OCT are aligned in relation to the tomograms $T_1$ to $T_n$. In general, when a plurality of tomograms of OCT is captured, there is a tendency that the imaging range varies in the Z-axis direction due to the movement of the eye, etc. The use of a correction coefficient of the image, etc., to modify the variations in the Z-axis direction is called "alignment" here, and it is assumed that the process of "alignment" is already completed for the volumetric images handled below.

In S210, the image obtaining unit 100 has obtained a plurality of OCT volumetric images stored in the data server 20 and has stored the images in the storage unit 120. The plurality of obtained OCT volumetric images are a group of OCT volumetric images that are captured at different date/time from the same examined eye of the same patient diagnosed as, for example, glaucoma and that are associated with temporal changes. The data server 20 holds the OCT volumetric images in association with the captured date/time. The image obtaining unit 100 reads out the images from the data server 20 along with the captured date/time and stores the images in the storage unit 120. The control unit 200 selects an OCT volumetric image captured at the earliest time among the plurality of OCT volumetric images stored in the storage unit 120.

In S220, the detection unit 150 extracts a retina layer region from the OCT volumetric image selected by the control unit 200. The retina region can be extracted by, for example, simple binarization processing to the tomogram. An empirically determined fixed value may be used as a threshold in the binarization processing, and either a discriminant analysis or a P-tile method may be used to determine the threshold in accordance with the inputted OCT image.

The detection unit 150 segments layers of the retina region to detect an inner limiting membrane, a nerve fiber layer, an RPE boundary, etc. Specifically, a smoothing filter is first applied to the target tomogram $T_k$ to remove noise components. An edge detection filter is applied to the image after the noise smoothing to generate an edge-enhanced image. Each "A scan line" of the edge-enhanced image is scanned, and pixels with values higher than a certain threshold are selected. The uppermost (on the side with smaller Z-axis values) pixel in the tomogram among the selected pixels is a pixel indicating the inner limiting membrane. If there is a plurality of pixels selected in each "A scan line", the lowermost (on the side with larger Z-axis values) pixel of the tomogram other than the pixel determined as the inner limiting membrane indicates the RPE boundary. It should be noted that although the inner limiting membrane is set in the "A scan line" with only one selected pixel, the RPE is not set.

However, the method of detecting the inner limiting membrane and the RPE is not limited to this, and for example, the detection unit 150 may use a histogram of the image or texture information to detect the inner limiting membrane and the RPE. Although the detection unit 150 selects the pixels greater than the threshold in the edge-enhanced image in the present embodiment, the method is not limited to this. For example, the detection unit 150 may calculate a gradient from the brightness profile and use the gradient as an index for the detection. Alternatively, the detection unit 150 may calculate a feature amount from the brightness information and set the feature amount as an input to use a discriminator for the detection.

The detection unit 150 detects RPE ends from the RPE boundary 1. As shown by 320 of FIG. 3, there are regions R1 and R3 where the RPE boundary calculated for each tomogram $T_k$ exists and a region R2 where the boundary is cut out. The detection unit 150 sets both ends of the region as RPE ends, the region in which the boundary of the RPE is discontinuous as shown in R2, and the "A scan lines" continuously exist in the regions R1 and R2. The detection unit 150 connects the RPE ends found in each tomogram $T_k$ in the volumetric images to set an approximate value of an optic papilla periphery.

In S230, the model construction unit 160 constructs a model of the sclera from the RPE boundary and the RPE ends detected by the detection unit 150. The model of the sclera does not include information inside the sclera, but the model can include information of the shape of the optic papilla periphery equivalent to an Elschnig ring and the boundary of the sclera and a chroid coat. Therefore, the model construction unit 160 uses the RPE ends detected in S220 as the shape of the optic papilla periphery and the RPE boundary detected in step S220 as the shape of the surface of the sclera to construct the model of sclera. Specifically, the model construction unit 160 moves parallel to a curved surface formed by pixels detected as the RPE boundary in the OCT volumetric image in the Z-axis direction to approximate the shape of the surface of the sclera. In general, it is known that the thickness of the chroid coat is about 0.2 mm, and the thickness is about the same as the thickness of the retina (0.1 mm to 0.4 mm). Therefore, the model construction unit 160 calculates an average value d of the distance between the inner limiting membrane and the RPE boundary (that is, region where the RPE boundary exists) detected in S220 to move parallel the curved surface detected as the PRE boundary in the direction opposite to the inner limiting membrane by an amount of d.

The model construction unit 160 further moves parallel to the RPE ends calculated for each tomogram $T_k$ in step S220 as the optic papilla periphery by an amount of d, and the section connected in the volumetric image is set as the approximate value of the optic papilla periphery. In S240, the combining unit 170 combines the model of the sclera constructed by the model construction unit 160 with the OCT volumetric images. The combining of the model denotes the providing of a label of a sclera when each voxel of 3D constructed from the OCT volumetric images shown in FIG. 3 corresponds to the region of the sclera model constructed in S230.

Figure 4:
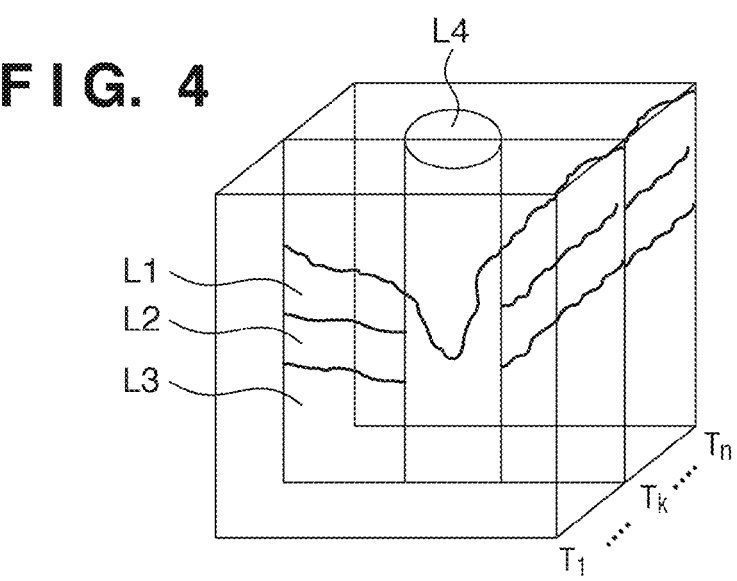
FIG. 4 is a diagram showing an example of volumetric images combined with a model of the sclera.

The combining unit 170 also provides the label of the retina to the voxel corresponding to the retina region (that is, region between the inner limiting membrane and the RPE) detected in S220 and provides a label of a chroid coat when the voxel corresponds to the region between the RPE and the sclera. FIG. 4 shows a relationship between the volumetric images and the label. In this case, L1 denotes a retina region, L2 denotes a chroid coat region, and L3 denotes a sclera region. The region surrounded by the RPE ends (where the RPE boundary is not detected on the "A scan lines") is designated as a papilla region L4.

There are structural changes in the nerve fiber layer, etc., in the retina region and the papilla region in the follow-up of glaucoma, while the sclera scarcely changes. This fact is focused on here. Specifically, the combining unit 170 not only combines the model of sclera constructed in S230 with the OCT volumetric images used to create the model, but also combines the model of sclera with all OCT volumetric images related to the same eye of the same patient obtained as follow-up. In this regard, the control unit 200 obtains a plurality of OCT volumetric images stored in S210 in the storage unit 120. The combining unit 170 combines the model of the sclera constructed by the model construction unit 160 in S230 with the plurality of acquired OCT volumetric images.

In this case, high accuracy cannot be attained if the OCT volumetric images after the progression of disease and the model of sclera constructed based on the OCT volumetric images captured at the initial stage of disease in S230 are directly combined. This is because it is known that the retina region in the OCT volumetric images is associated with large structural changes along with the progression of disease. In such a case, the combining unit 170 executes an overlay process between the OCT volumetric images after the temporal changes and the OCT volumetric images at the previous capturing. Based on the result, the combining unit 170 further combines the OCT volumetric images after the temporal changes with the sclera model based on the volumetric images in which the OCT volumetric images at the previous capturing and the sclera model are combined.

Figure 5:
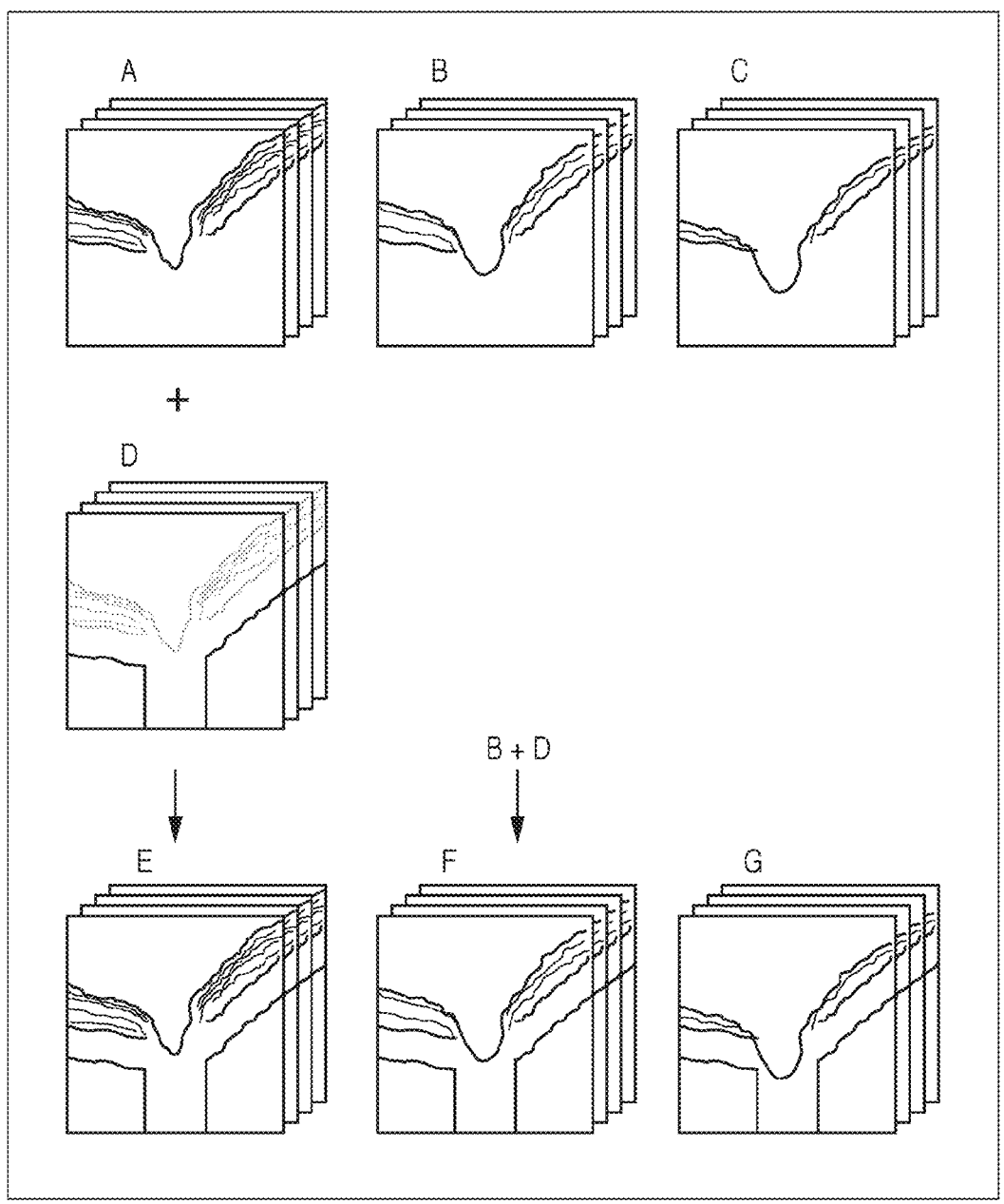
FIG. 5 is a diagram showing an exemplary method of combining temporally changed OCT volumetric images with a model of the sclera.

FIG. 5 shows a specific process. In FIG. 5, A, B, and C denote OCT volumetric images of the same eye of the same patient. The images B are images one year after capturing of the images A, and the images C are images after three years. Reference character D denotes a model of the sclera created based on the volumetric images A, and reference character E denotes volumetric images obtained by combining A and D. The sclera model D does not change. In view of direct combining of the volumetric images B after one year and D as well as the volumetric images C and D, there are larger structural changes in the retinal layer in C than in A. Particularly, the RPE ends, etc., may be changed. Therefore, combining of C and D is difficult. Thus, the combining unit 170 first executes an overlay process between C and B to calculate the relative position of C to B. The combining unit 170 further calculates the relative position of B and D from combined images F obtained by combining B and D. Since the relative position of D and the relative position of C are calculated based on B, the combining unit 170 can combine D and C, and the combining unit 170 creates combined volumetric images G.

In S250, the display unit 130 displays the OCT volumetric images including the model of the sclera combined and created by the combining unit 170 on a display device such as a display, not shown. The result output unit 140 saves in the data server 20 information of the combined volumetric images created in the procedure of the foregoing steps.

Figure 6:
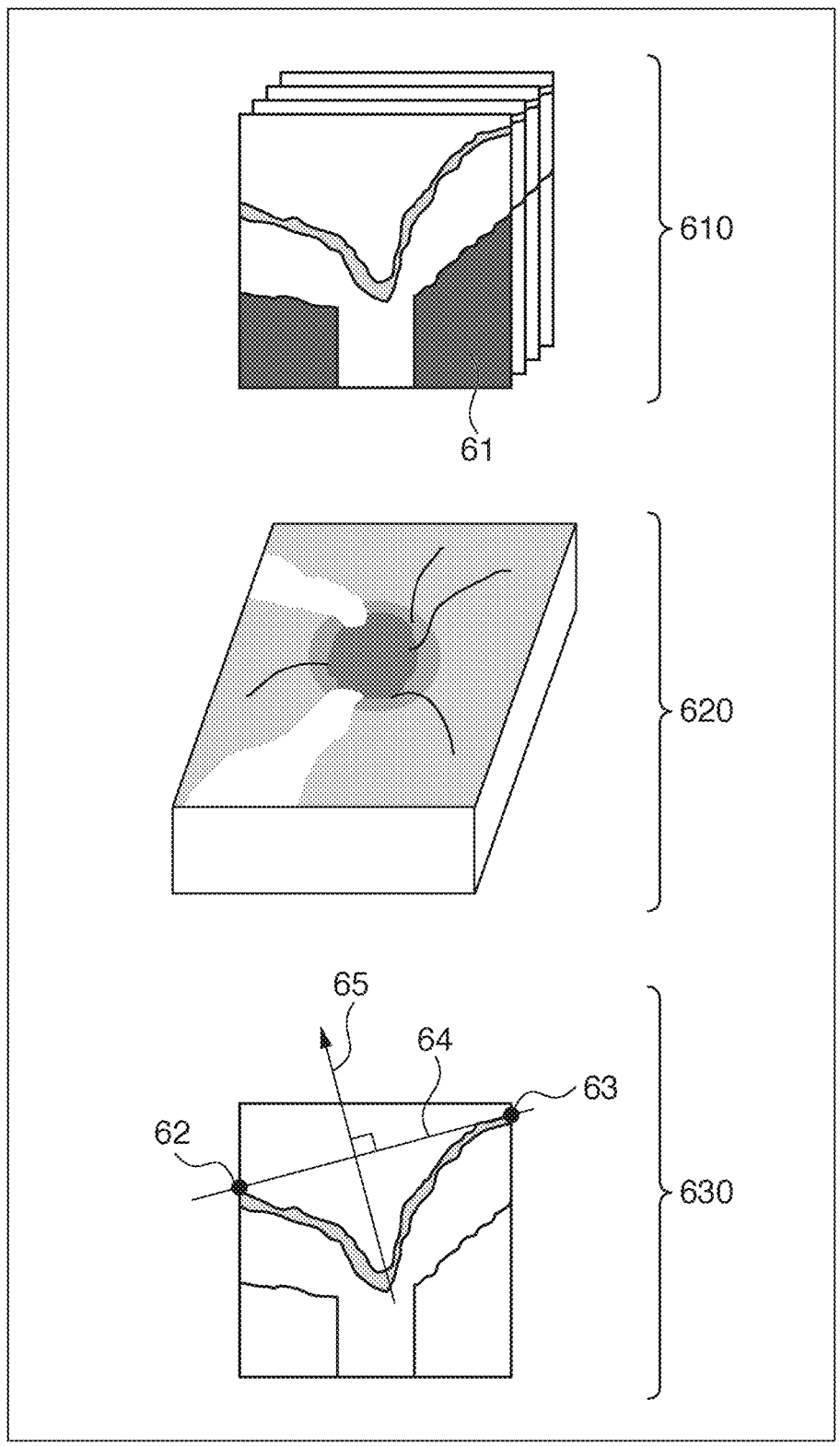
FIG. 6 is a diagram showing an example of display of volumetric images combined with a model of the sclera.

FIG. 6 shows a specific example of display of the combined volumetric images. In the diagnosis of glaucoma, it is important to see the distribution of the thickness of the nerve fiber layer in comparison with the optic papilla periphery. Therefore, the display unit 130 particularly extracts only the nerve fiber layer part in the retina region detected in S220 and sets single-color information to the voxel equivalent to the region. The display unit 130 further sets a small value to opacity a of the nerve fiber layer region at combining so that the sclera region indicating the optic papilla periphery can be checked. As shown in 610 of FIG. 6, the display unit 130 sets 1 to the opacity a in relation to the sclera region 61 so that complete opacity is set.

As shown in 620 of FIG. 6, the display unit 130 uses the created volumetric images to perform volume-rendering display. In the present embodiment, the display unit 130 sets a viewpoint on a position as shown in 630 of FIG. 6 to present an image of observing the fundus by a slit lamp, etc. Specifically, the display unit 130 obtains points 62 and 63 where the inner limiting membrane touches the edges of the volumetric image at four sections of the volumetric image to obtain a direction 65 orthogonal to a straight line 64 connecting two opposing sections and sets a viewpoint on the vector.

In the example, the display unit 130 uses the segmentation result of the retina layer region to provide single-color information only to the nerve fiber layer to perform volume rendering. However, to utilize the brightness information obtained from the OCT volumetric images, the display unit 130 can utilize low opacity and brightness information of OCT in relation to the retina layer region and the papilla region to provide an opacity of 1 to the sclera region to perform volume rendering.

The display unit 130 can further use the inner limiting membrane to perform surface rendering display to three-dimensionally illustrate the shape of the cup of the C/D ratio (cup/disc ratio) that is important in the diagnosis of glaucoma. In this case, the display unit 130 uses detection points of the inner limiting membrane obtained in S220 to create a polygonal surface. The display unit 130 can further translucently display the polygonal set to present the polygonal set along with the sclera shape subjected to opacity display to stereoscopically display the cup and the disc. If the display unit 130 displays, as a thickness map on the polygonal surface, thickness information of the nerve fiber layer upon 3D display, the thickness information of the nerve fiber layer can be obtained along with the shape of the inner limiting membrane. Therefore, the display is more effective for the diagnosis.

Although an example of using the OCT volumetric images combined with the sclera model to perform the volume rendering display or the surface rendering display has been described, the display method is not limited to this. For example, the volume rendering and the surface rendering may be combined. Specifically, a display method may be implemented, in which only the nerve fiber layer is subjected to the volume rendering, and the sclera is subjected to the surface rendering.

The image processing apparatus 10 uses various display methods based on the volumetric images combined with the model of sclera to display follow-up data. As shown in FIG. 5, the image processing apparatus 10 can combine the same sclera model with the OCT volumetric images captured for the follow-up to illustrate the changes in the retina region and the optic papilla region.

Figure 7:
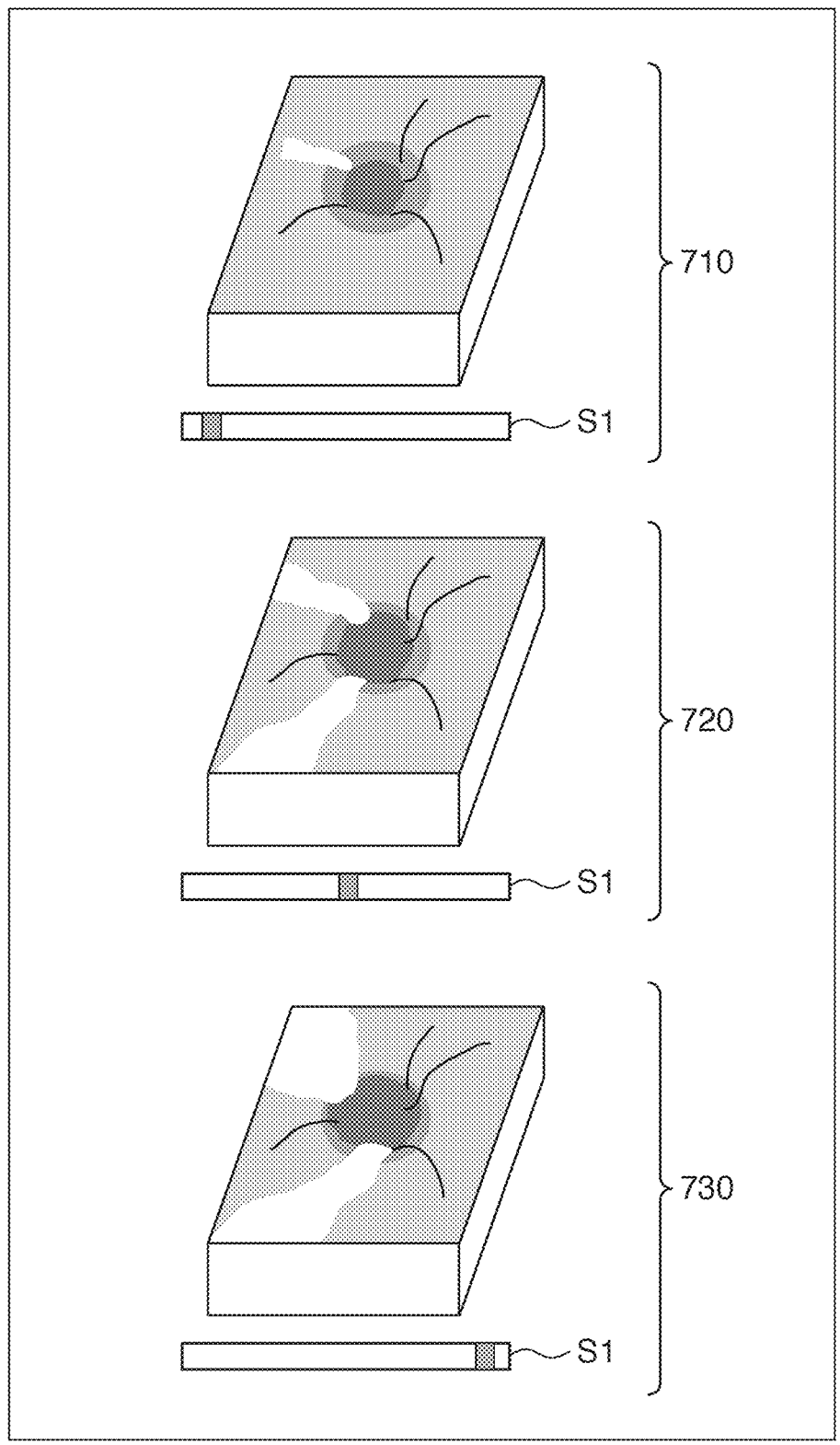
FIG. 7 is a diagram showing an example of display of follow-up images using the volumetric images combined with the model of the sclera.

Specifically, the image processing apparatus 10 attaches a scroll bar S1 on a 3D display screen as shown in images 710, 720, and 730 of FIG. 7 to display images combined with the OCT volumetric images captured at different times as the bar is scrolled. The scroll bar S1 is sequentially set as shown by 610, 620, and 630 of FIG. 6 to display, for example, E, F, and G of FIG. 5 in chronological order. As for the 3D display, the display type or the viewpoint is changed to display the state most suitable for the observation, and the time change can be scrolled. The changes in the retinal layer caused by disease can be explicitly displayed.

According to the configuration, the image processing apparatus 10 can construct a three-dimensional model of the sclera from the information related to the sclera as a physical structure of the disc and combine the three-dimensional models in the volumetric images of OCT. The image processing apparatus 10 can use the combined volumetric images to simultaneously present the detailed information of the retina, such as the nerve fiber layer, and the entire image including the depth information of the optic papilla including the disc. For example, the image processing apparatus 10 can simultaneously present the information of the retina layer with noticeable changes associated with the progression of disease and the optic papilla periphery with a stable structure so that the presentation is effective in the follow-up of glaucoma using the OCT volumetric images. As a result, there is an advantage that the user of the image processing apparatus 10 can observe the 3D information of the optic papilla in comparison with the information of the disc.

Second Embodiment

The information of the RPE boundary and the RPE ends obtained from the OCT volumetric images is used to construct the model of the sclera in the first embodiment. However, the RPE ends provide the approximate value of the optic papilla periphery only when there are no findings of peripapillary atrophies (PPA), etc., and it is difficult to construct the model of the sclera only from the OCT volumetric images after the progression of disease. In a second embodiment, a case of using image data of an image other than the OCT volumetric images, a fundus image here, to construct a more accurate model to create the model of the sclera will be described.

Figure 8:
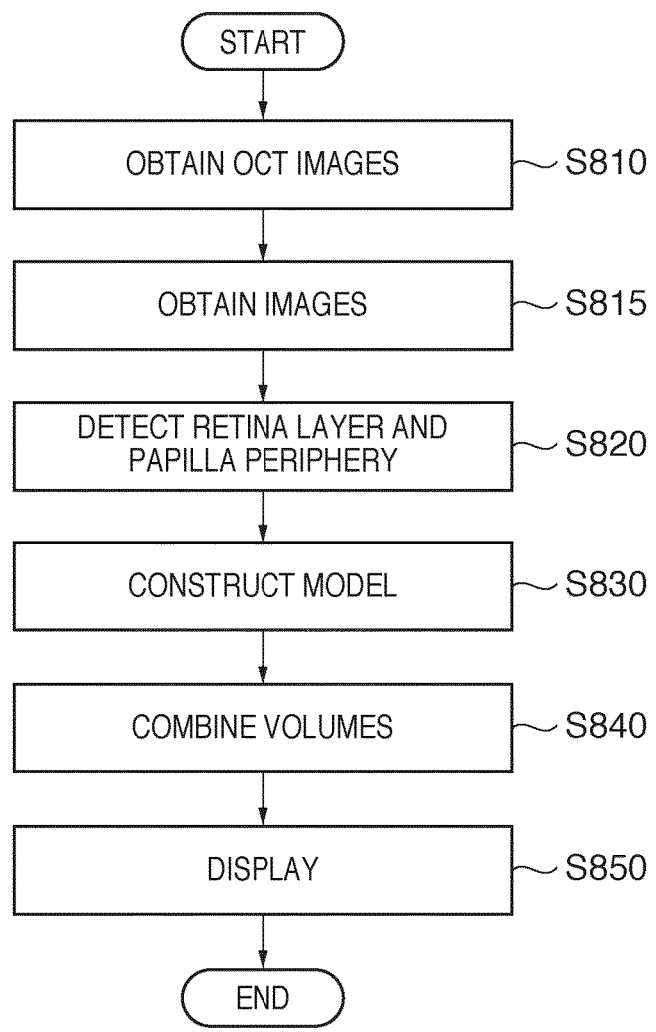
FIG. 8 is a flow chart showing an exemplary processing procedure of an image processing apparatus 10 according to a second embodiment.

Hereinafter, a processing procedure of the image processing apparatus 10 of the present embodiment will be described with reference to the flow chart of FIG. 8. Steps S810, S840, and S850 are the same as steps S210, S240, and S250 of the first embodiment, respectively, and the description thereof will not be repeated. It is assumed that a plurality of fundus images are associated with the capturing time and stored in the data server 20 along with the OCT volumetric images.

In S815, the image obtaining unit 100 obtains the plurality of fundus images stored in the data server 20 and stores the fundus images in the storage unit 120. The obtained fundus images are images acquired by capturing the same eye of the same patient as for the OCT volumetric images obtained in step S810. The control unit 200 selects a fundus image captured at a time closest to the OCT volumetric image selected in S810 among the plurality of fundus images saved in the storage unit 120.

In S820, the detection unit 150 extracts the retina layer region from the image data of the OCT volumetric image selected by the control unit 200 to segment the layers and detects the RPE boundary. The detection unit 150 further detects the optic papilla periphery from the fundus image selected by the control unit 200.

The detection of the retina layer region from the OCT volumetric image is the same as in S220, and the description thereof will not be repeated. The detection unit 150 combines generally known binarization processing, edge enhanced filter, etc., to extract the optic papilla periphery from the image data of the fundus image.

In S830, the model construction unit 160 uses the RPE boundary and the optic papilla periphery extracted by the detection unit 150 to construct the model of the sclera. The RPE boundary and the optic papilla periphery are extracted from two types of images, the OCT volumetric image and the fundus image, respectively. Therefore, two types of extracted parts are integrated by overlaying two types of images. Specifically, the model construction unit 160 accumulates, in the Z-axis direction of 310 of FIG. 3, the brightness values obtained from the image data of the OCT volumetric images to create an accumulated image. The accumulated image is an image in which the retina is observed from the surface, just like the fundus image. Therefore, the model construction unit 160 overlays the accumulated image and the fundus image. In this case, the model construction unit 160 extracts blood vessels from the fundus image and the accumulated image and overlays the images based on the alignment of the blood vessels.

The model construction unit 160 integrates the RPE boundary extracted from the OCT volumetric images and the optic papilla periphery included in the fundus image based on the overlay of the OCT volumetric images and the fundus image. The model construction unit 160 creates an approximate surface of the RPE boundary based on the RPE boundary detected in S820. Parts close to the papilla where the RPE boundary is not detected, i.e., the RPE ends where the RPE boundary is discontinuous detected in the first embodiment, cannot be detected. Therefore, the optic papilla periphery included in the fundus image is used to identify the RPE ends. For the parts close to the papilla where the RPE boundary is not detected, the model construction unit 160 extrapolates a surface from the surrounding to the identified RPE ends to obtain an approximate plane of the entire RPE boundary. The model construction unit 160 overlays the optic papilla periphery extracted from the fundus over the approximate plane. Since the fundus image does not include three-dimensional information, the position of the detected optic papilla periphery in the Z-axis direction is not determined. However, the optic papilla periphery can be confirmed by limiting the position to the RPE approximate surface.

The model construction unit 160 uses the integrated RPE boundary and the optic papilla periphery to create the model of the sclera. As in S230, the model construction unit 160 moves the integrated RPE boundary and the optic papilla periphery in the Z-axis direction of the OCT volumetric image by an amount of d to set the model of sclera.

Although an example of using the fundus image and the OCT volumetric images to construct the model of sclera has been illustrated, the method of constructing the model of the sclera is not limited to this, and images from other modalities, such as SLO, can also be used.

Furthermore, different parts may be extracted and integrated from OCT volumetric images obtained by using light sources with different wavelengths or by setting different focus positions by adjusting the coherence gate. In this way, a more accurate model of the sclera can be constructed by integrating information from various images.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-083401, filed Mar. 31, 2010 which is hereby incorporated by reference herein in its entirety.

What is claimed is:

1. An image processing apparatus comprising:
   a storage unit configured to store a plurality of tomographic images in relation to the fundus of an examined eye of a patient;
   a detection unit configured to detect a boundary of retinal pigment epithelium and an inner limiting membrane from each of the plurality of tomographic images and to detect a part where the boundary of the retinal pigment epithelium is discontinuous;
   a determination unit configured to determine a surface of a sclera model for each of the plurality of tomographic images by use of the detected boundary of the retinal pigment epithelium and the detected inner limiting membrane;
   a generation unit configured to generate a sclera model including an optic papilla periphery by use of the determined surface of the sclera model and the detected part where the boundary of the retinal pigment epithelium is discontinuous;
   a combining unit configured to combine each of the plurality of tomographic images and the sclera model to generate a combined image; and
   a display unit configured to display the combined image generated by the combining unit.

2. An image processing apparatus comprising:
   a storage unit configured to store a plurality of tomographic images and a fundus image in relation to a fundus of an examined eye of a patient;
   a detection unit configured to detect a boundary of retinal pigment epithelium and an inner limiting membrane of the examined eye from each of the plurality of tomographic images;
   a detection unit configured to detect an optic papilla periphery from the fundus image;
   an identification unit configured to identify the boundary of the retinal pigment epithelium and a part where the boundary is discontinuous in the examined eye, by aligning the fundus image and the plurality of tomographic images and using the optic papilla periphery detected from the fundus image;
   a determination unit configured to determine a surface of a sclera model for each of the plurality of tomographic images by use of the identified boundary of the retinal pigment epithelium and the detected inner limiting membrane;
   a generation unit configured to generate a sclera model including the optic papilla periphery by use of the determined surface of the sclera model and the identified part where the boundary is discontinuous;
   a combining unit configured to combine each of the plurality of tomographic images and the sclera model to generate a combined image; and
   a display unit configured to display the combined image generated by the combining unit.

3. The apparatus according to claim 1, wherein the determination unit is configured to move a representation of the detected boundary of the retinal pigment epithelium in a direction away from a representation of the detected inner limiting membrane by a distance between the detected retinal pigment epithelium and the detected inner limiting membrane to determine the surface of the sclera model.

4. The apparatus according to claim 2, wherein the identification unit is configured to use the identified boundary of the retinal pigment epithelium and the detected optic papilla periphery to overlay an accumulated image, in which brightness values obtained from the plurality of tomographic images are accumulated in a direction from the inner limiting membrane to the boundary of the retinal pigment epithelium, and the fundus image to perform the aligning performed by the identification unit.

5. An image processing apparatus comprising:
   a storage unit configured to store an image including optic papilla of an examined eye;
   an obtaining unit configured to obtain an image of a retina layer and an optic papilla periphery of the examined eye from the stored image;
   a model construction unit configured to construct a model of a sclera of the examined eye based on the obtained image of the retina layer and optic papilla periphery;
   a combining unit configured to combine the constructed model of the sclera with the stored image; and
   a display control unit configured to display the combined image on a display unit.

6. An image processing apparatus comprising:
   a storage unit configured to store a plurality of images including optic papilla of an examined eye;
   an obtaining unit configured to obtain an image of a retina layer and an image of an optic papilla periphery of the examined eye from the stored images;
   a model construction unit configured to construct a model of the sclera of the examined eye based on the obtained images of the retina layer and the optic papilla periphery;

a combining unit configured to combine the constructed model of the sclera with the plurality of images of the examined eye; and a display control unit configured to display the plurality of images combined with the same sclera model on a display unit.

7. The apparatus according to claim 5, wherein the model construction unit is configured to use a shape of a retinal pigment epithelium boundary of the examined eye and end points of the optic papilla of the retinal pigment epithelium boundary of the examined eye to construct the model of the sclera.

8. A control method of an image processing apparatus, the method comprising:

storing, by a storage unit, a plurality of tomographic images in relation to a fundus of an examined eye of a patient;

detecting, by a detection unit, a boundary of retinal pigment epithelium and an inner limiting membrane from each of the plurality of tomographic images, and a part where the boundary of the retinal pigment epithelium is discontinuous;

determining, by a determination unit, a surface of a sclera model for each of the plurality of tomographic images by use of the detected boundary of the retinal pigment epithelium and the detected inner limiting membrane;

generating, by a generation unit, a sclera model including an optic papilla periphery by use of the determined surface of the sclera model and the detected part where the boundary of the retinal pigment epithelium is discontinuous;

combining, by a combining unit, each of the plurality of tomographic images and the sclera model to generate a combined image; and displaying, by a display unit, the combined image generated in the combining step.

9. A control method of an image processing apparatus, the method comprising:

storing, by a storage unit, a plurality of tomographic images and a fundus image in relation to a fundus of an examined eye of a patient;

detecting, by a detection unit, a boundary of retinal pigment epithelium and an inner limiting membrane from each of the plurality of tomographic images;

detecting, by a detection unit, an optic papilla periphery from the fundus image;

identifying, by an identification unit, the boundary of the retinal pigment epithelium and a part where the boundary is discontinuous in the examined eye, by aligning the fundus image and the plurality of tomographic images and using the optic papilla periphery detected from the fundus image;

determining, by a determination unit, a surface of a sclera model for each of the plurality of tomographic images by use of the identified boundary of the retinal pigment epithelium and the detected inner limiting membrane;

generating, by a generation unit, a sclera model including the optic papilla periphery, by use of the determined surface of the sclera model and the identified part of the epithelium where the boundary is discontinuous;

combining, by a combining unit, each of the plurality of tomographic images and the sclera model to generate a combined image; and displaying, by a display unit, the combined image generated in the combining step.

10. A program stored in a non-transitory computer-readable storage medium for causing a computer to execute the method according to claim 8.

11. An image processing apparatus comprising:

an extraction unit configured to extract a first layer from one or more tomographic images of an examined eye;

a determination unit configured to determine a discontinuous point of the first layer; and a generating unit configured to generate a shape model of a second layer extracted from the tomographic images based on information about the first layer and a periphery shape model of optic papilla based on the discontinuous point of the first layer and a discontinuous point of the second layer, the second layer being different from the first layer, wherein the tomographic images are a plurality of tomographic images obtained by capturing a plurality of B-scan images of the fundus of the examined eye, and wherein the shape model of the second layer and the periphery shape model of an optic papilla each have three dimensions.

12. The apparatus according to claim 11, wherein the shape model of the second layer is generated by moving parallel to a location of the first layer by a certain amount.

13. The apparatus according to claim 12, wherein the certain amount is determined based on a distance between the first layer and a third layer different from both the first and second layers.

14. The apparatus according to claim 11, further comprising a combining unit configured to generate a first combined image in which the shape model of the second layer is combined with the tomographic images.

15. The apparatus according to claim 11, wherein the first layer is retinal pigment epithelium or a boundary thereof, the second layer is a sclera or a boundary thereof, and a third layer is an inner limiting membrane or a boundary thereof.

16. An image processing apparatus comprising:

an extraction unit configured to extract a first layer from one or more tomographic images of an examined eye;

a generating unit configured to generate a shape model of a second layer extracted from the tomographic images based on information about the first layer, the second layer being different from the first layer;

a unit configured to obtain a second tomographic image of the examined eye captured at a different time, from the one or more tomographic images; and a combining unit configured to generate a first combined image in which the shape model of the second layer is combined with the tomographic images and a second combined image in which the shape model of the second layer is aligned with the second tomographic image.

17. The apparatus according to claim 16, wherein the extraction unit is further configured to determine a discontinuous point of the first layer.

18. The apparatus according to claim 17, wherein the generating unit is further configured to generate a periphery shape model of an optic papilla based on the discontinuous point of the first layer and a discontinuous point of the second layer.

19. The apparatus according to claim 18, wherein the tomographic images are a plurality of tomographic images obtained by capturing a plurality of B-scan images of the fundus of the examined eye, and wherein the shape model of the second layer and the periphery shape model of the optic papilla each have three dimensions.

20. The apparatus according to claim 16, further comprising a display control unit configured to simultaneously display the first combined image and the second combined image.

21. A control method of an image processing apparatus, the method comprising the steps of:

extracting, by an extraction unit, a first layer from one or more tomographic images of an examined eye;

determining, by a determination unit, a discontinuous point of the first layer; and generating, by a generating unit, a shape model of a second layer from the tomographic images based on information about the first layer and a periphery shape model of an optic papilla based on the discontinuous point of the first layer and a discontinuous point of the second layer, the second layer being different from the first layer, wherein the tomographic images are a plurality of tomographic images obtained by capturing a plurality of B-scan images of the fundus of the examined eye, and wherein the shape model of the second layer and the periphery shape model of the optic papilla each have three dimensions.

22. A program stored in a non-transitory computer-readable storage medium for causing a computer to execute the method according to claim 21.

23. A control method of an image processing apparatus, the method comprising the steps of:

obtaining, by an obtaining unit, a first tomographic image and a second tomographic image of an examined eye, the second tomographic image being captured at a different time from the first tomographic image;

extracting, by an extraction unit, a first layer from the first tomographic image;

generating, by a generating unit, a shape model of a second layer extracted from the first tomographic image based on information about the first layer, the second layer being different from the first layer; and generating, by a combining unit, a first combined image in which the shape model of the second layer is combined with the first tomographic image and a second combined image in which the shape model of the second layer is aligned with the second tomographic image.

24. A program stored in a non-transitory computer-readable storage medium for causing a computer to execute the method according to claim 23.

* * * * *